| (12) | United States Patent | (10) Patent No.: | US 10,813,780 B2 |
|---|---|---|---|
| | Solaun et al. | (45) Date of Patent: | Oct. 27, 2020 |

(54) INTRALUMINAL IMPLANT DELIVERY SYSTEM AND METHOD

(71) Applicant: DePuy Synthes Products, Inc., Raynham, MA (US)

(72) Inventors: Daniel Solaun, Raynham, MA (US); David Blumenstyk, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 141 days.

(21) Appl. No.: 16/058,932

(22) Filed: Aug. 8, 2018

(65) Prior Publication Data

US 2020/0046533 A1 Feb. 13, 2020

(51) Int. Cl.
*A61F 2/962* (2013.01)
*A61F 2/82* (2013.01)
*A61F 2/95* (2013.01)

(52) U.S. Cl.
CPC ............. *A61F 2/962* (2013.01); *A61F 2/82* (2013.01); *A61F 2002/9511* (2013.01)

(58) Field of Classification Search
CPC .......... A61F 2/962; A61F 2/95; A61F 2/9517; A61F 2/966; A61M 25/02; A61B 17/12109; A61B 17/12022
See application file for complete search history.

(56) References Cited

U.S. PATENT DOCUMENTS

| 6,391,037 | B1 | 5/2002 | Greenhalgh |
|---|---|---|---|
| 6,773,448 | B2 | 8/2004 | Kusleika et al. |
| 6,849,081 | B2 | 2/2005 | Sepetka et al. |
| 7,147,618 | B2 | 12/2006 | Kurz |
| 7,419,498 | B2 | 9/2008 | Opolski et al. |
| 7,785,361 | B2 | 8/2010 | Nikolchev et al. |
| 7,942,894 | B2 | 5/2011 | West |
| 8,911,487 | B2 | 12/2014 | Bennett et al. |
| 9,232,992 | B2 | 1/2016 | Heidner |
| 9,532,792 | B2 | 1/2017 | Galdonik et al. |
| 9,532,873 | B2 | 1/2017 | Kelley |
| 9,533,344 | B2 | 1/2017 | Monetti et al. |
| 9,539,011 | B2 | 1/2017 | Chen et al. |
| 9,539,022 | B2 | 1/2017 | Bowman |
| 9,539,122 | B2 | 1/2017 | Burke et al. |
| 9,539,382 | B2 | 1/2017 | Nelson |

(Continued)

FOREIGN PATENT DOCUMENTS

WO 98/11846 A1 3/1998

OTHER PUBLICATIONS

Extended European Search Report issued in corresponding European Patent Application No. 19 19 0496 dated Jan. 3, 2020.

*Primary Examiner* — Richard G Louis (74) *Attorney, Agent, or Firm* — Troutman Pepper Hamilton Sanders LLP (57) ABSTRACT

Systems, devices, and methods for retracting a pull wire from a hypotube can include positioning a pull wire having an engagement bump on its proximal end within a channel of a device and sliding the pull wire proximally through a channel of a device by moving grippers of the device proximally to engage and slide the bump. Subsequent distal movement of the grippers can result in the grippers disengaging the bump without disturbing the position of the pull wire or causing the pull wire to move distally.

17 Claims, 7 Drawing Sheets

(56) References Cited

U.S. PATENT DOCUMENTS

| | | | |
|---|---|---|---|
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,104 B2 | 2/2017 | Beckham et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,322 B2 | 7/2017 | Dias et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman | |
| 9,770,577 B2 | 9/2017 | Li | |
| 9,775,621 B2 | 10/2017 | Tompkins et al. | |
| 9,775,706 B2 | 10/2017 | Peterson | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman | |
| 9,833,252 B2 | 12/2017 | Sepetka | |
| 9,833,604 B2 | 12/2017 | Lam | |
| 9,833,625 B2 | 12/2017 | Waldhauser et al. | |
| 2003/0083613 A1* | 5/2003 | Schaer | A61B 18/1492 |
| | | | 604/95.04 |
| 2006/0064151 A1 | 3/2006 | Guterman | |
| 2007/0179520 A1 | 8/2007 | West | |
| 2008/0281350 A1 | 11/2008 | Sepetka | |
| 2010/0324649 A1 | 12/2010 | Mattsson | |
| 2011/0238147 A1* | 9/2011 | Bennett | A61M 25/01 |
| | | | 623/1.11 |
| 2012/0029607 A1 | 2/2012 | McHugo et al. | |
| 2012/0283768 A1 | 11/2012 | Cox et al. | |
| 2013/0046338 A1* | 2/2013 | Suzuki | A61B 10/04 |
| | | | 606/205 |
| 2014/0135812 A1 | 5/2014 | Divino et al. | |
| 2014/0200607 A1 | 7/2014 | Sepetka et al. | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu | |
| 2017/0027640 A1 | 2/2017 | Kunis et al. | |
| 2017/0027692 A1 | 2/2017 | Bonhoeffer | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero | |
| 2017/0079680 A1 | 3/2017 | Bowman | |
| 2017/0079766 A1 | 3/2017 | Wang | |
| 2017/0079767 A1 | 3/2017 | Leon-Yip | |
| 2017/0079812 A1 | 3/2017 | Lam et al. | |
| 2017/0079817 A1 | 3/2017 | Sepetka | |
| 2017/0079819 A1 | 3/2017 | Pung et al. | |
| 2017/0079820 A1 | 3/2017 | Lam et al. | |
| 2017/0086851 A1 | 3/2017 | Wallace | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Grandfield | |
| 2017/0100183 A1 | 4/2017 | Iaizzo | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein | |
| 2017/0165454 A1 | 6/2017 | Tuohy | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0252064 A1 | 9/2017 | Staunton | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder | |
| 2017/0290593 A1 | 10/2017 | Cruise et al. | |
| 2017/0290654 A1 | 10/2017 | Sethna | |
| 2017/0296324 A1 | 10/2017 | Argentine | |
| 2017/0296325 A1 | 10/2017 | Marrocco et al. | |
| 2017/0303939 A1 | 10/2017 | Greenhalgh | |
| 2017/0303942 A1 | 10/2017 | Greenhalgh et al. | |
| 2017/0303947 A1 | 10/2017 | Greenhalgh | |
| 2017/0303948 A1 | 10/2017 | Wallace et al. | |
| 2017/0304041 A1 | 10/2017 | Argentine | |
| 2017/0304097 A1 | 10/2017 | Corwin et al. | |
| 2017/0304595 A1 | 10/2017 | Nagasrinivasa | |
| 2017/0312109 A1 | 11/2017 | Le | |
| 2017/0312484 A1 | 11/2017 | Shipley et al. | |
| 2017/0316561 A1 | 11/2017 | Helm et al. | |
| 2017/0319826 A1 | 11/2017 | Bowman | |
| 2017/0333228 A1 | 11/2017 | Orth et al. | |
| 2017/0333236 A1 | 11/2017 | Greenan | |
| 2017/0333678 A1 | 11/2017 | Bowman | |
| 2017/0340383 A1 | 11/2017 | Bloom et al. | |
| 2017/0348014 A1 | 12/2017 | Wallace | |
| 2017/0348514 A1 | 12/2017 | Guyon et al. | |
| 2017/0367857 A1 | 12/2017 | Bennett et al. | |

* cited by examiner

INTRALUMINAL IMPLANT DELIVERY SYSTEM AND METHOD

FIELD OF INVENTION

The present invention generally relates to medical devices, and more particularly, to deploying intraluminal implants.

BACKGROUND

Numerous intravascular implant devices are well known in the field. Many are deployed mechanically, via systems that combine one or more catheters and wires for delivery. Examples of implants that may be delivered mechanically include embolic elements, stents, grafts, drug delivery implants, etc. Some obstetric and gastrointestinal implants may also be implanted via similar systems that combine one or more catheters and wires. Devices that may be released or deployed by mechanical means vary greatly in design but can employ a similar delivery catheter and wire system. Many such catheter-based delivery systems include a wire for retention of the implant in the catheter until the time for release of the device. These systems are then actuated by retracting or pulling the wire relative to the catheter. Such a wire is referred to herein as a "pull wire".

Precise deployment of the implant is crucial for the successful treatment of vascular and luminal abnormalities. For some applications, complications can arise if a pull wire is pulled proximally and then subsequently pushed distally.

It is an object of the invention to provide systems, devices, and methods for reducing complications in such applications.

SUMMARY

Disclosed herein are various exemplary systems, devices, and methods of the present invention that can address the above needs. Examples in general can include an implantation device having a pull wire extending from a proximal end of a hypotube, and the pull wire can have an engagement bump or extending portion near a proximal end of the pull wire. Examples in general can additionally or alternatively include a device for retracting the pull wire from the hypotube. The retracting device can have a channel or groove in which the pull wire and engagement bump can be positioned and movable grippers or retractors that can be moved to engage the engagement bump of the pull wire. Once the engagement bump is engaged, if the grippers are subsequently moved proximally, the grippers can pull the pull wire proximally through the channel, or if the grippers are subsequently moved distally, the grippers can disengage the engagement bump without disturbing the position of the pull wire or causing the pull wire to move distally.

In one example, a system for deploying an implant can include a hypotube, a pull wire, an engagement bump positioned on the pull wire, a groove sized to slidably receive the engagement bump, and a movable gripper. The pull wire can be positioned within a lumen of the hypotube extending proximally out of the hypotube lumen, and the engagement bump can be positioned near a proximal end of the pull wire. The gripper can be movable in a proximal direction and a distal direction such that the gripper can engage the engagement bump upon movement in the proximal direction and disengage the engagement bump upon movement in the distal direction. A movement of the gripper in the proximal direction can solely engage the engagement bump of the pull wire and no other surface of the pull wire. The system can further include a space maintained between the gripper and a circumference of the pull wire.

The engagement bump can slide through a first length of the groove in the proximal direction upon a first movement of the gripper in the proximal direction, the engagement bump can remain stationary in relation to the groove upon a second movement of the gripper in the distal direction, and the engagement bump can slide through a second length of the groove in the proximal direction upon a third movement of the gripper in the proximal direction.

The system can further include a track through which the gripper can move. The track can have a parallel segment positioned parallel to the channel and an extending segment positioned distal the parallel segment and extending away from the channel in at least a lateral direction.

The gripper can extend the pull wire proximally from the proximal end of the hypotube upon a movement of the gripper in the proximal direction, and the pull wire can remain stationary in relation to the hypotube upon a movement of the gripper in the distal direction. The gripper can also be movable in a lateral direction, and a movement of the gripper in the proximal direction can result in a first lateral movement approaching the pull wire, and a movement of the gripper in the distal direction can result in a second lateral movement retreating from the pull wire. The system can further include a spring applying a spring force to the gripper in the distal direction.

The groove can further include a distal end engaging the proximal end of the hypotube and preventing proximal movement of the hypotube in relation to the groove. The groove can be sized to inhibit a lateral movement of the engagement bump.

The system can further include a first and second gripper, each movable in the distal direction and the proximal direction, each engaging the engagement bump upon movement in the proximal direction and disengaging the engagement bump upon movement in the distal direction. The first and second gripper can be joined for simultaneous movement in the proximal direction and the distal direction.

An example device for retracting a pull wire from a hypotube can include a receptacle having a channel and a distal surface and a retractor coupled to the receptacle having an engagement surface. The channel of the receptacle can slidably receive a pull wire, and the distal surface of the receptacle can engage a proximal end of a hypotube. The retractor can be movable in a proximal direction and a distal direction parallel to the channel, and the engagement surface can be positioned approximate the channel to engage an extending portion of the pull wire. A proximal movement of the retractor can extract the pull wire from the proximal end of the hypotube, thereby extending the pull wire into the channel. A subsequent distal movement of the retractor can disengage the extending portion of the pull wire such that pull wire remains stationary in relation to the hypotube.

The device can further include a track having a parallel segment positioned parallel to the channel. The retractor can be coupled to the track such that the parallel segment inhibits lateral movement of the retractor. The track can further comprise an extending segment positioned distal the parallel segment that extends away from the channel, and the retractor can be movable in at least a lateral direction when moved along the extending segment of the track.

The device can further include a spring applying spring force to the retractor in the distal direction.

The device can further include a first retractor movable within a first track and second retractor movable within a second track. The first and second tracks can be shaped as mirror images of each other about an axis defined by the length of the channel, and the first and second retractors can be coupled for simultaneous movement.

An example method of manipulating an implant delivery system can include the steps of providing an implantation device having a pull wire and a hypotube, positioning an engagement bump on the pull wire near a proximal end of the pull wire, providing a retracting device having a channel and a gripper, positioning the pull wire within the channel, engaging a proximal end of the hypotube with a distal surface of the retracting device, moving the gripper to engage the engagement bump, pulling the gripper and the engaged engagement bump proximally through the channel thereby retracting the pull wire proximally from the proximal end of the hypotube, moving the gripper distally to disengage the engagement bump, and maintaining a stationary position of the pull wire in relation to the channel in response to the moving of the gripper distally.

The method can further include the steps of providing a parallel track segment positioned parallel to the channel, coupling the gripper to the parallel track segment, moving the gripper through the parallel track segment parallel to the channel, and inhibiting lateral movement of the gripper by the coupling of the parallel track segment. The retracting device can have two grippers: the aforementioned gripper and second gripper, and the method can further include the steps of positioning the grippers on opposite sides of the channel and coupling the grippers to each other for simultaneous movement.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

An implant delivery system can include a pull wire extending from a catheter or hypotube having an engagement bump or extending portion at the proximal end of the pull wire. The pull wire can be positioned within a groove or channel of a retracting device and can be controllably slid through the groove while the hypotube is prevented from moving through the groove.

The retracting device can include tracks positioned on opposite sides of the groove that together make a Y-shape, and grippers or retractors can be guided by the tracks along the pull wire groove. In their initial position, the grippers can be positioned on the wide, distal end of the Y-track. The grippers can be translated proximally through the Y-track, moving closer to the pull wire until the grippers contact the engagement bump, but not the pull wire. The grippers can be further translated proximally through a parallel portion of the Y-track, pulling the engagement bump (and therefore the pull wire) proximally in the process.

The retracting device can include springs attached to the grippers that can provide a spring force pushing the grippers distally, and the grippers can be joined together for simultaneous translation by a slider. When the slider is released, the grippers can move distally to their initial position on the wide, distal end of the track. Movement of the grippers distally can disengage the engagement bump without disturbing the pull wire. Even in a scenario wherein the grippers are prematurely released, the grippers can move distally without causing distal translation of the pull wire.

Figure 1:
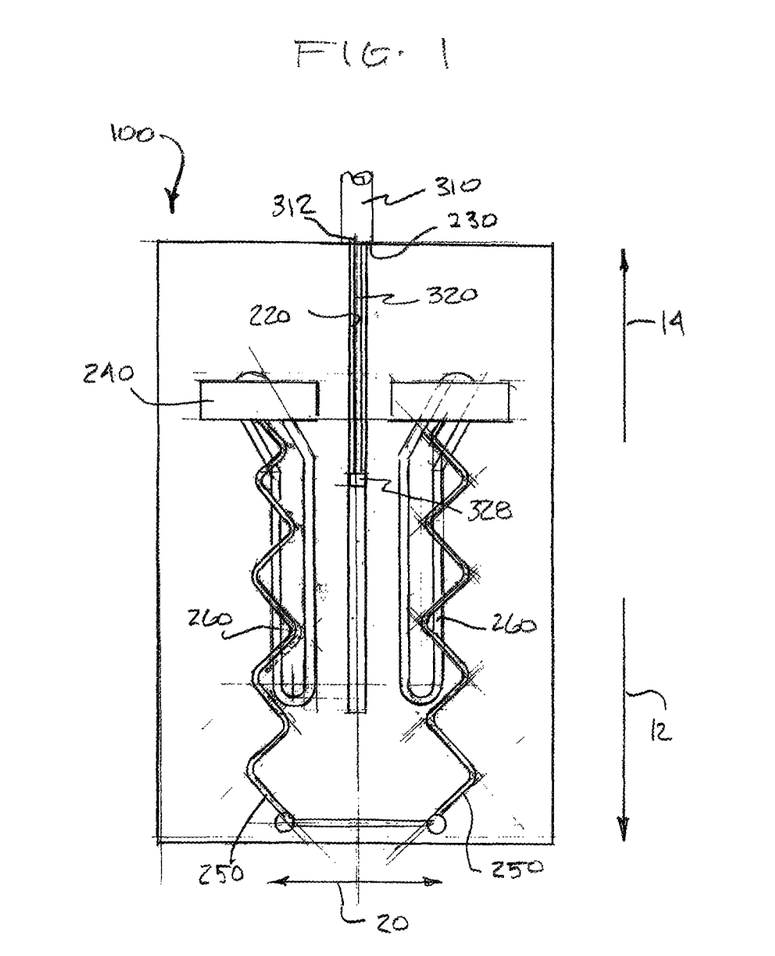
FIG. 1 is a drawing of an exemplary system of the present invention.

An example system 100 for deploying an implant is illustrated in FIG. 1. The system 100 can include an implantation device having a hypotube 310 and a pull wire 320 and a retractor device having a channel or groove 220 and one or more grippers or retractors 240. The pull wire 320 can extend proximally from a lumen 316 of the hypotube 310. The pull wire 320 can be positioned in the channel 220, and the hypotube 310 can be positioned to have a proximal surface 312 abutting the retractor device, preventing the hypotube 310 from travelling proximally through the channel 220. The pull wire 320 can have an engagement bump 328 positioned on or near the proximal end 324 of the pull wire 320, and the engagement bump 328 can be sized to slide through the channel 220. FIG. 1 depicts grippers 240 positioned in a starting position, pushed in a distal direction 14 by springs 250. As shown, the grippers 240 can be positioned within tracks 260 and can be pulled in a proximal direction 12 through the tracks 260 with the springs 250 providing an opposing spring force. The tracks 260 can form a Y-shape such that when the grippers 240 are pulled proximally, the grippers 240 approach the pull wire 320 and engage the engagement bump 328 of the pull wire 320. The grippers 240 can then be pulled proximally parallel to the channel 220, maintaining a space between the grippers 240 and the pull wire 320. Once released, the grippers 240 can disengage the engagement bump 328 and return to the starting position without disturbing the positioning of the pull wire 320.

Figure 2A:
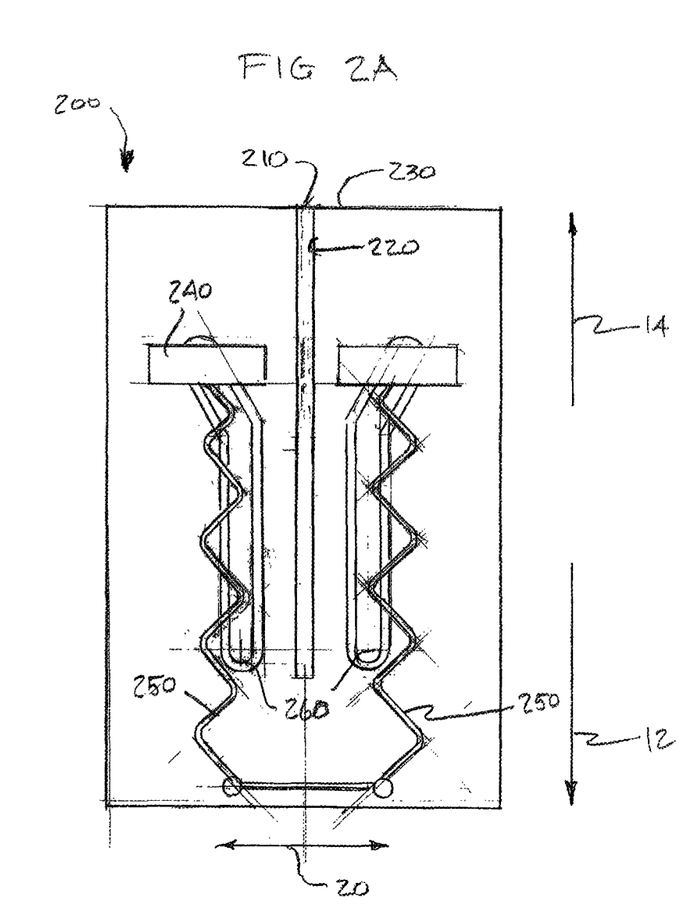
FIG. 2A is a drawing of an exemplary device of the present invention.

FIG. 2A depicts an exemplary retractor device 200. The retractor device can have a receptacle 210 for receiving a pull wire 320 of an implantation device.

Figure 2B:
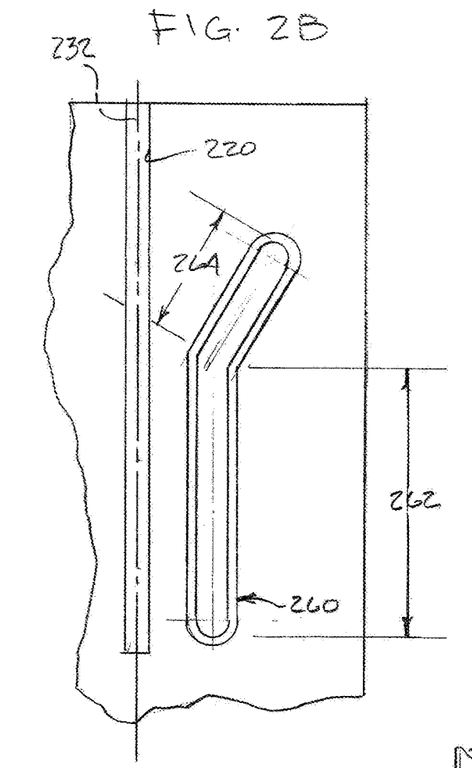
FIG. 2B is a close-up drawing of a portion of the exemplary device of FIG. 2A depicting a track and a channel.

FIG. 2B is a close-up drawing of a portion of the exemplary device of FIG. 2A depicting a track 260 and a channel 220. The track 260 can have a parallel segment 262 travelling substantially parallel to the channel 220 and an extending segment 264 that extends in at least a lateral direction 20 away from the channel 220. As shown the extending section can also extend distally to form half of a Y-shape. The device of FIG. 2A can have two tracks 260 positioned opposite the channel 220, mirrored about a central axis 232 to form two halves of the Y-shape.

Figure 3:
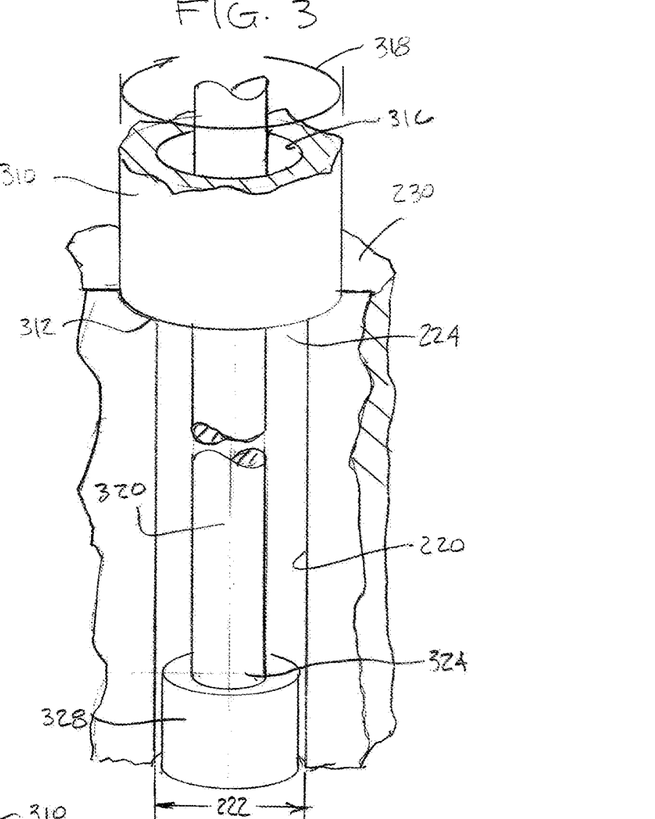
FIG. 3 is a close-up drawing of a portion of an exemplary system of the present invention depicting a pull wire having an engagement bump extending from a hypotube and positioned within a channel.

FIG. 3 is a close-up drawing of a portion of an exemplary system. As shown, a pull wire 320 can extend from a hypotube lumen 316 and be positioned within a channel 220. The channel 220 can have a width 222 sized to slidably receive an engagement bump 328 at a proximal end 324 of the pull wire 320 while simultaneously stopping the hypotube 310 from travelling proximally. The hypotube 310 can have a circumference 318 that is sized larger than the channel 220, and the retraction device can have a distal surface 230 near the distal end 224 of the channel 220 so that when the pull wire 320 is positioned in the channel 220, a proximal end 312 of the hypotube 310 can abut the distal surface 230 of the retraction device, thereby preventing proximal movement of the hypotube 310 in relation to the channel 220.

Figure 4:
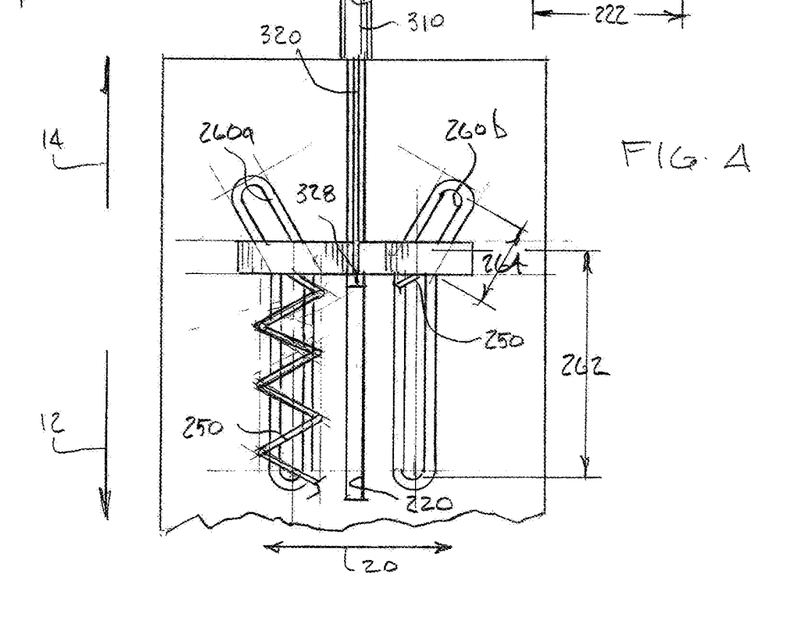
FIG. 4 is a drawing of an exemplary system of the present invention illustrating a proximal movement of a pair of grippers to engage an engagement bump of a pull wire.

FIG. 4 is a drawing illustrating a pair of grippers 240a, 240b positioned to engage an engagement bump 328 of a pull wire 320. A first and second gripper can be moved along a first and second track 260a,260b such that the tracks form a Y-shape. Each track can have an extending segment 264 that extends away from the channel 220 and a parallel segment 262 that extends parallel to the channel 220. In FIG. 4, the grippers 240a, 240b are shown positioned at the intersection of the extending segments 264 and the parallel segments 262. In this position the grippers 240a,240b can engage the engagement bump 328, and further proximal movement of the grippers 240a,240b can cause the pull wire 320 to travel proximally through the channel 220.

Figure 5A:
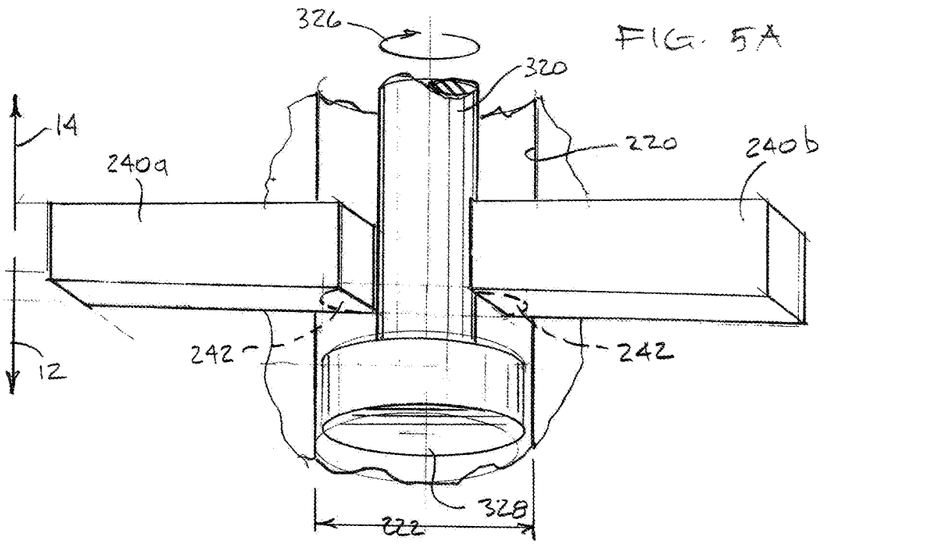
FIG. 5A is a close-up drawing of a portion of an exemplary system of the present invention depicting a pair of grippers positioned near an engagement bump on a pull wire.

FIG. 5A is a close-up drawing depicting a pair of grippers 240a, 240b positioned near an engagement bump 328 on a pull wire 320. Each gripper can have an engagement surface 242 that can engage the engagement bump 328 when the grippers 240a,240b are pulled in the proximal direction 12. As shown, the pull wire 320 can have a circumference 326 that is narrower than the engagement bump 328 and grippers 240a,240b can approach the pull wire 320 to engage the engagement bump 328 without making contact to the pull wire 320. The channel 220 can have a width 222, and the circumference 326 of the pull wire 320 can be sized such that the grippers 240a,240b can extend into the channel 220 to engage the engagement bump 328 without making contact to the pull wire 320.

Figure 5B:
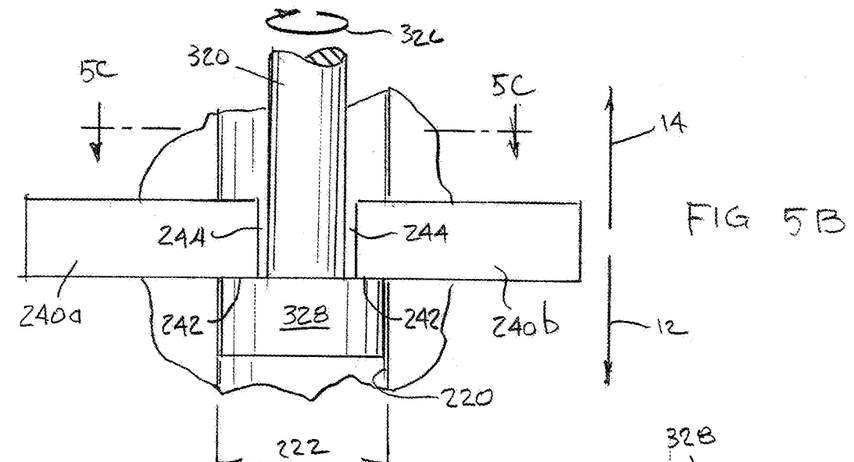
FIG. 5B is a close-up drawing of the portion of the exemplary system of FIG. 5A depicting the pair of grippers engaging the engagement bump.

FIG. 5B is a close-up drawing depicting the pair of grippers 240a,240b engaging the engagement bump 328. The grippers 240a,240b have been moved in the proximal direction 12 in relation to FIG. 5A. A space 244 is maintained between the grippers 240a,240b and the pull wire circumference 326 such that the grippers 240a,240b solely engage the engagement bump 328 and do not otherwise engage the pull wire 320.

Figure 5C:
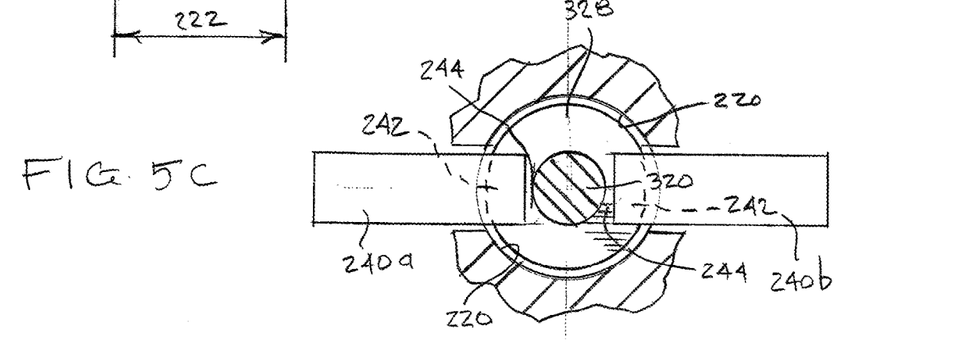
FIG. 5C is a cross-sectional view of the portion of the exemplary system of FIG. 5B.

FIG. 5C is a cross-sectional view of the system depicted in FIG. 5B. The pull wire 320 is shown centrally located with the engagement bump 328 extending circumferentially from the pull wire 320, and the channel 220 is shown partially surrounding the engagement bump 328. The grippers 240a,240b are shown overlapping the engagement bump 328 such that each gripper has an engagement surface 242 defined by the overlap of the gripper with the engagement bump 328. A gap 244 is shown positioned between the grippers 240a,240b and the pull wire 320 such that the grippers 240a,240b do not contact the pull wire 320.

Figure 6:
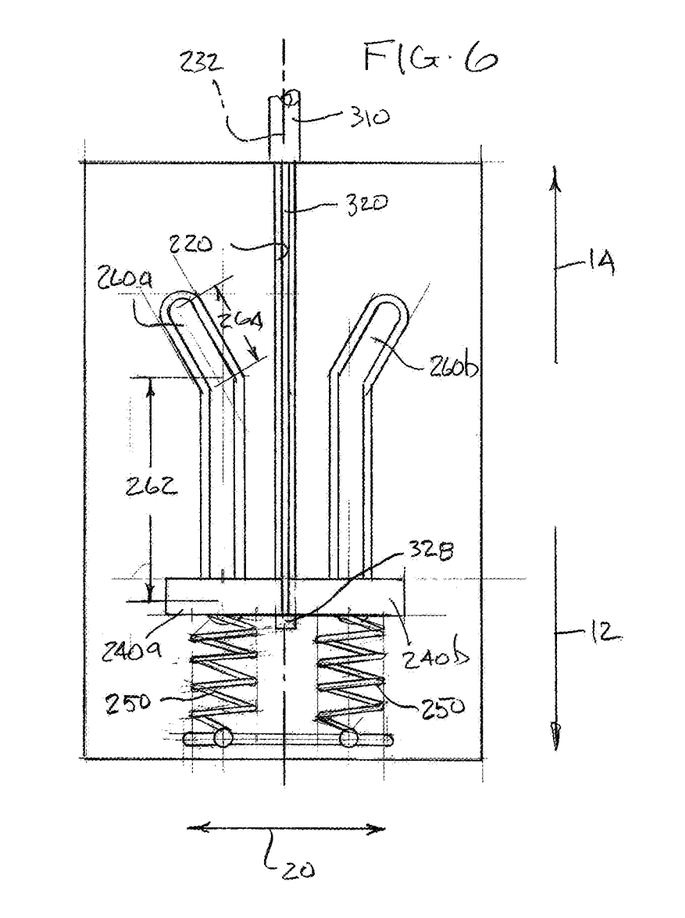
FIG. 6 is a drawing of an exemplary system of the present invention depicting the pull wire fully retracted.

FIG. 6 is a drawing depicting a pull wire 320 fully retracted. A first and second gripper can be moved proximally through a first and second track 260a,260b to retract the pull wire 320 from a hypotube 310. FIG. 6 shows the grippers 240a,240b each positioned a proximal end of their respective tracks 260a,260b.

Figure 7:
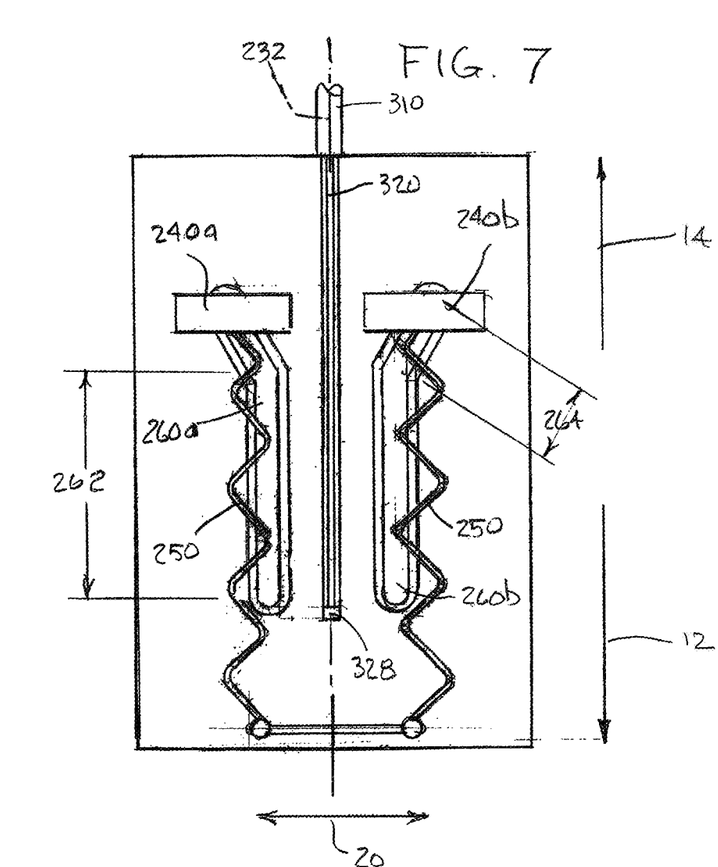
FIG. 7 is a drawing of an exemplary system of the present invention depicting a pair of grippers returned to their original position following the retraction of the pull wire.

FIG. 7 is a drawing depicting a pair of grippers 240a,240b returned to their original position following the retraction of the pull wire 320. When the grippers 240a,240b are released, the springs 250 can move each gripper through each track 260a,260b to their original position while the pull wire 320 remains fully retracted.

Figures 8A, 8B, 8C:
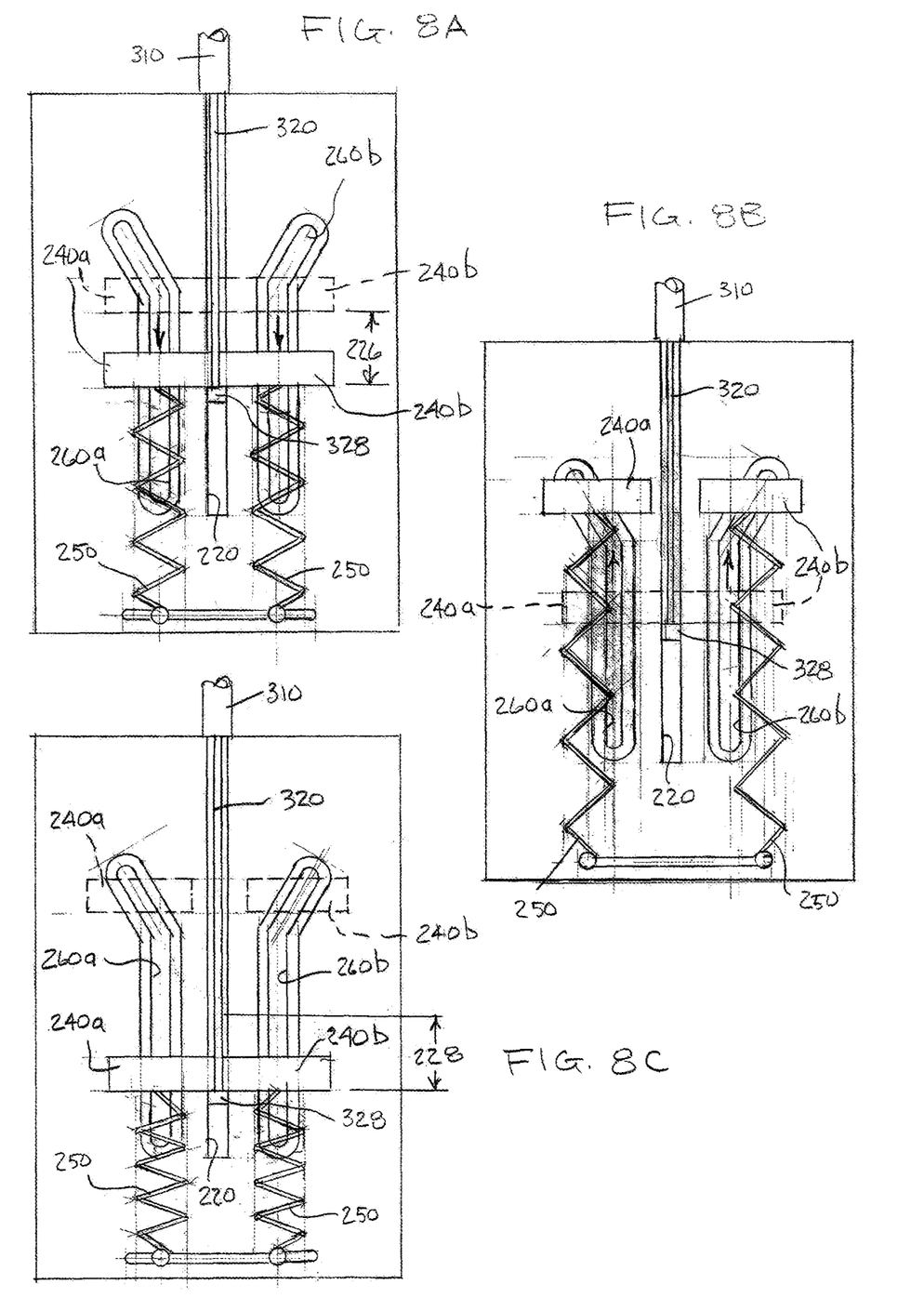
FIGS. 8A to 8C are drawings of an exemplary system of the present invention depicting (respectively) a first movement of the grippers proximally, a second movement of the grippers distally, and a third movement of the grippers proximally.

FIGS. 8A to 8C are drawings depicting a series of movements of the grippers 240a,240b. FIG. 8A depicts a first movement of the grippers 240a,240b in the proximal direction 12 along a parallel segment 262 of each respective track 260a,260b. The grippers 240a,240b can be engaged with the engagement bump 328 causing the pull wire 320 to slide through a first length 226 of the channel 220. FIG. 8B depicts a second movement of the grippers 240a,240b in the distal direction 14. Distal movement of the grippers 240a, 240b can disengage the engagement bump 328, and the pull wire 320 can remain in the partially retracted position as depicted in FIG. 8A. FIG. 8C depicts a third movement of the grippers 240a,240b in the proximal direction 12. If the grippers 240a,240b are moved further proximally than as shown in FIG. 8A, the grippers 240a,240b can engage the engagement bump 328 and move the pull wire 320 proximally through a second length 228 of the wire.

Figure 9:
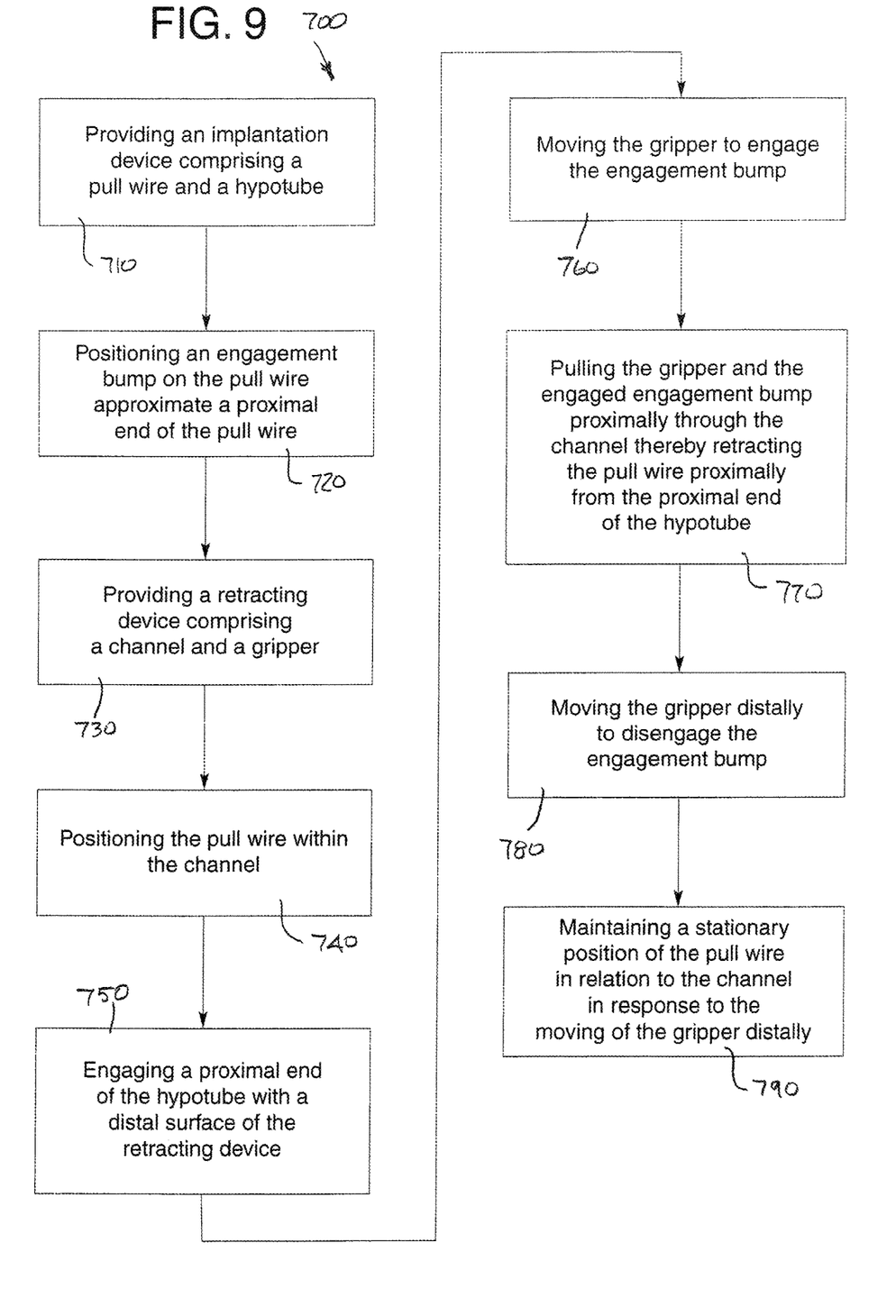
FIGS. 9 to 11 are a flow diagrams outlining method steps that may be performed according to the present invention.

FIG. 9 is a flow diagram 700 outlining method steps that can be performed during implant delivery. In step 710 an implantation device having a pull wire and a hypotube can be provided. In step 720 an engagement bump can be positioned on the pull wire approximate a proximal end of the pull wire. In step 730 a retracting device having a channel and a gripper can be provided. In step 740 a pull wire can be positioned within the channel. In step 750 a proximal end of the hypotube can engage a distal surface of the retracting device. In step 760 the gripper can be moved to engage the engagement bump. In step 770 the gripper and the engaged engagement bump can be pulled proximally through the channel thereby retracting the pull wire proximally from the proximal end of the hypotube. In step 780 the gripper can be moved distally to disengage the engagement bump. In step 790 the pull wire can remain in a stationary position in relation to the channel as the gripper is moved distally.

Figure 10:
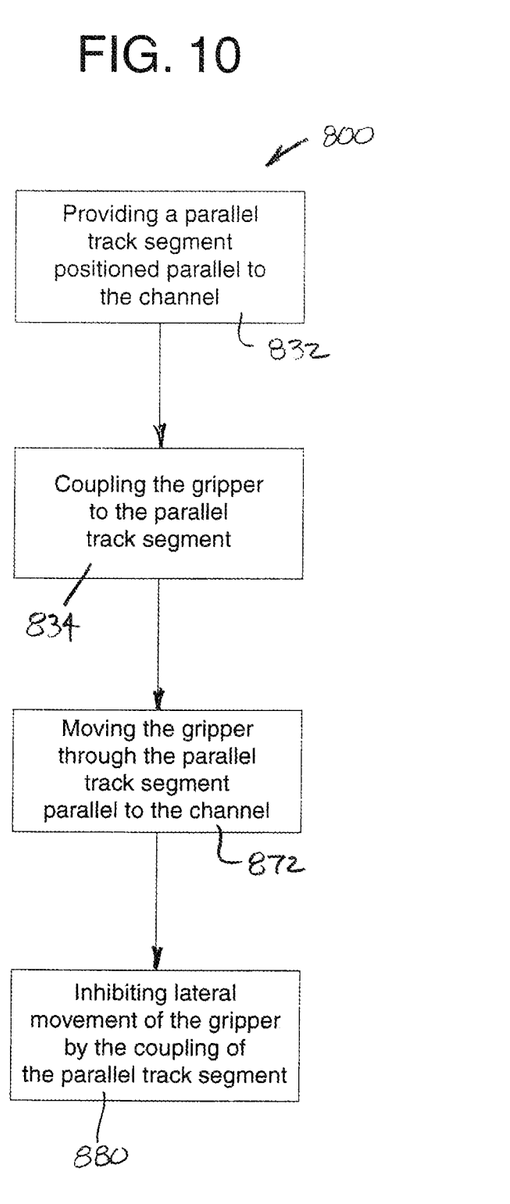

FIG. 10 is a flow diagram 800 outlining method steps that can be performed in addition to or in place of method steps outlined in FIG. 9. In step 832 a parallel track segment can be positioned parallel to the channel. In step 834 the gripper can be coupled to the parallel track segment. In step 872 the gripper can be moved parallel to the channel through the parallel track segment. In step 880 the coupling of the gripper to the parallel track segment can inhibit lateral movement of the gripper.

Figure 11:
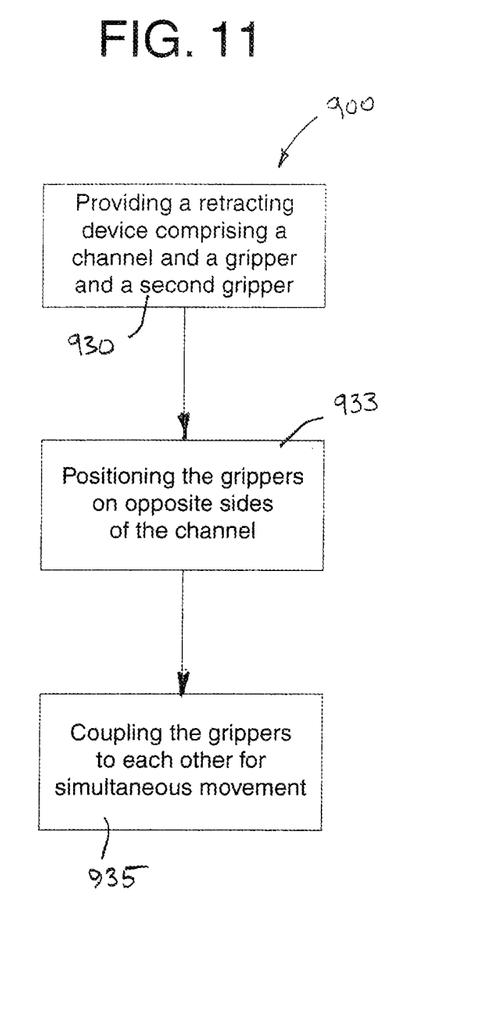

FIG. 11 is a flow diagram 900 outlining method steps that can be performed in addition to or in place of method steps outlined in FIGS. 9 and 10. In step 930 a retracting device comprising a channel and a pair of grippers can be provided. In step 933 the grippers can be positioned opposite each other on opposite sides of the channel. In step 935 the grippers can be coupled to each other for simultaneous movement.

The descriptions contained herein are examples of embodiments of the invention and are not intended in any way to limit the scope of the invention. As described herein, the invention contemplates many variations and modifications of the implantation deployment system, including alternative structures for the engagement bump such as a ball or hook or other shape providing similar functionality, alternative means for guiding the grippers in relation to the channel, alternative means for receiving and preventing proximal movement of the hypotube, alternative means of allowing the engagement bump to pass proximally through the gripper space when placing in the groove, etc. These modifications would be apparent to those having ordinary skill in the art to which this invention relates and are intended to be within the scope of the claims which follow.

The invention claimed is:

1. A system for deploying an implant comprising:
 a hypotube comprising a lumen therethrough and a proximal end;
 a pull wire positioned within the lumen and extending proximal the proximal end of the hypotube, the pull wire comprising a proximal end and a circumference;
 an engagement bump positioned on the pull wire approximate the proximal end of the pull wire and extending beyond the circumference of the pull wire;
 a groove sized to slidably receive the engagement bump; and
 a gripper movable in a distal direction and a proximal direction, the gripper engaging the engagement bump upon movement in the proximal direction and disengaging the engagement bump upon movement in the distal direction, and
 wherein,
  the engagement bump slides through a first length of the groove in the proximal direction upon a first movement of the gripper in the proximal direction,
  the engagement bump remains stationary in relation to the groove upon a second movement of the gripper in the distal direction, and
  the engagement bump slides through a second length of the groove in the proximal direction upon a third movement of the gripper in the proximal direction.

2. The system of claim 1 wherein a movement of the gripper in the proximal direction solely engages the engagement bump.

3. The system of claim 1 further comprising a space maintained between the gripper and the circumference of the pull wire.

4. A system for deploying an implant comprising:
 a hypotube comprising a lumen therethrough and a proximal end;
 a pull wire positioned within the lumen and extending in a proximal direction from the proximal end of the hypotube, the pull wire comprising a proximal end and a circumference;
 an engagement bump positioned on the pull wire approximate the proximal end of the pull wire and extending beyond the circumference of the pull wire;
 a channel sized to slidably receive the engagement bump;
 a gripper movable in a distal direction and a proximal direction, the gripper engaging the engagement bump upon movement in the proximal direction and disengaging the engagement bump upon movement in the distal direction; and
 a track through which the gripper is movable, the track comprising:
  a parallel segment positioned parallel to the channel; and
  an extending segment positioned distal the parallel segment and extending away from the channel in at least a lateral direction.

5. The system of claim 4 wherein the gripper extends the pull wire proximally from the proximal end of the hypotube upon a movement of the gripper in the proximal direction and wherein the pull wire remains stationary in relation to the hypotube upon a movement of the gripper in the distal direction.

6. The system of claim 1 wherein the groove further comprises a distal end engaging the proximal end of the hypotube and preventing proximal movement of the hypotube in relation to the groove.

7. The system of claim 1 wherein the groove is sized to inhibit a lateral movement of the engagement bump.

8. The system of claim 1 further comprising a spring applying a spring force to the gripper in the distal direction.

9. The system of claim 1,
 wherein said gripper is a first gripper in a pair of grippers, the pair of grippers comprising the first gripper and a second gripper, the first and second gripper being each movable in the distal direction and the proximal direction, the first and second gripper each engaging the engagement bump upon movement in the proximal direction and disengaging the engagement bump upon movement in the distal direction.

10. The system of claim 9 wherein the first and second gripper are joined for simultaneous movement in the proximal direction and the distal direction.

11. A system for deploying an implant comprising:
 a hypotube comprising a lumen therethrough and a proximal end;
 a pull wire positioned within the lumen and extending in a proximal direction from the proximal end of the hypotube, the pull wire comprising a proximal end and a circumference;
 an engagement bump positioned on the pull wire approximate the proximal end of the pull wire and extending beyond the circumference of the pull wire;
 a channel sized to slidably receive the engagement bump; and
 a gripper movable in a distal direction and a proximal direction, the gripper engaging the engagement bump upon movement in the proximal direction and disengaging the engagement bump upon movement in the distal direction,
  wherein the gripper is movable in a lateral direction, and a movement of the gripper in the proximal direction results in a first lateral movement approaching the pull wire, and a movement of the gripper in the distal direction results in a second lateral movement retreating from the pull wire.

12. A device for retracting a pull wire from a hypotube, the device comprising:
 a receptacle comprising a channel for slidably receiving a pull wire and a distal surface for engaging a proximal end of a hypotube;

a retractor coupled to the receptacle movable in a proximal direction and a distal direction parallel to the channel comprising an engagement surface positioned approximate the channel for engaging an extending portion of the pull wire; and a track comprising a parallel segment positioned parallel to the channel,
wherein the parallel segment inhibits lateral movement of the retractor, and
wherein a proximal movement of the retractor extracts the pull wire from the proximal end of the hypotube extending the pull wire into the channel, and a subsequent distal movement of the retractor disengages the extending portion of the pull wire such that pull wire remains stationary in relation to the hypotube.

13. The device of claim 12 wherein,
the track further comprises an extending segment positioned distal the parallel segment and extending away from the channel, and
the retractor is movable in at least a lateral direction within the extending segment of the track.

14. The device of claim 13,
wherein said retractor is a first retractor in a pair of retractors, the pair of retractors comprising the first retractor and a second retractor,
wherein the first retractor is movable within a first track and the second retractor is movable within a second track,
wherein the first and second tracks are shaped as mirror images of each other about an axis defined by the length of the channel, and
wherein the first and second retractors are coupled for simultaneous movement.

15. The device of claim 12 further comprising a spring applying spring force to the retractor in the distal direction.

16. A method of manipulating an implant delivery system comprising the steps of:

providing an implantation device comprising a pull wire and a hypotube;
positioning an engagement bump on the pull wire approximate a proximal end of the pull wire;
providing a retracting device comprising a channel and a gripper;
providing a parallel track segment positioned parallel to the channel;
coupling the gripper to the parallel track segment;
positioning the pull wire within the channel;
engaging a proximal end of the hypotube with a distal surface of the retracting device;
moving the gripper to engage the engagement bump;
moving the gripper through the parallel track segment parallel to the channel;
inhibiting lateral movement of the gripper by the coupling of the parallel track segment;
pulling the gripper and the engaged engagement bump proximally through the channel thereby retracting the pull wire proximally from the proximal end of the hypotube;
moving the gripper distally to disengage the engagement bump; and
maintaining a stationary position of the pull wire in relation to the channel in response to the moving of the gripper distally.

17. The method of claim 16 wherein the retracting device comprises a pair of grippers, said gripper being a first gripper in the pair of grippers and the pair of grippers comprising a second gripper, the method further comprising the steps of:
positioning the first and second grippers on opposite sides of the channel from each other; and
coupling the first and second grippers to each other for simultaneous movement.

* * * * *